(12) United States Patent
Bergmann et al.

(10) Patent No.: US 12,262,740 B2
(45) Date of Patent: Apr. 1, 2025

(54) VAPORIZER CARTRIDGE AND INHALER COMPRISING SUCH A VAPORIZER CARTRIDGE

(71) Applicant: KÖRBER TECHNOLOGIES GMBH, Hamburg (DE)

(72) Inventors: Max Bergmann, Hamburg (DE); Lasse Cornils, Hamburg (DE); Matthias Giese, Tokyo (JP); Christian Hanneken, Hamburg (DE); Jan Jaklin, Fellbach (DE); Marc Kessler, Hamburg (DE); Michael Kleine Wächter, Lankau (DE); Thomas Müller, Hamburg (DE); Niklas Romming, Hamburg (DE); Rene Schmidt, Buchholz i.d.N. (DE); Christof Schuster, Hamburg (DE); Tobias Wuttke, Reinbek (DE)

(73) Assignee: KÖRBER TECHNOLOGIES GMBH, Hamburg (DE)

( * ) Notice: Subject to any disclaimer, the term of this patent is extended or adjusted under 35 U.S.C. 154(b) by 646 days.

(21) Appl. No.: 17/619,472

(22) PCT Filed: Jun. 17, 2020

(86) PCT No.: PCT/EP2020/066745
§ 371 (c)(1),
(2) Date: Dec. 15, 2021

(87) PCT Pub. No.: WO2020/254394
PCT Pub. Date: Dec. 24, 2020

(65) Prior Publication Data
US 2022/0400748 A1 Dec. 22, 2022

(30) Foreign Application Priority Data
Jun. 20, 2019 (DE) .......................... 102019116726.4

(51) Int. Cl.
*A24F 40/20* (2020.01)
*A24F 40/40* (2020.01)

(52) U.S. Cl.
CPC .............. *A24F 40/20* (2020.01); *A24F 40/40* (2020.01)

(58) Field of Classification Search
CPC .......... A24F 40/10; A24F 40/20; A24F 40/30; A24F 40/40; A24F 40/42; A24F 40/44;
(Continued)

(56) References Cited

U.S. PATENT DOCUMENTS

2017/0295844 A1* 10/2017 Thevenaz ................ A24F 40/46
2019/0183177 A1*  6/2019 Hubbard ................. A24F 40/30
(Continued)

FOREIGN PATENT DOCUMENTS

| DE | 102015115527 B3 | 1/2017 |
| DE | 102016120803 A1 | 5/2018 |
| WO | 2020065077 A1 | 4/2020 |

OTHER PUBLICATIONS

International Search Report dated Sep. 29, 2020; International Application PCT/EP2020/066745.

*Primary Examiner* — Joseph D. Boecker
*Assistant Examiner* — Brian T Khong
(74) *Attorney, Agent, or Firm* — Dinsmore & Shohl LLP

(57) ABSTRACT

An inhaler vaporizer cartridge includes a housing body with a flow channel, a liquid storage tank, and a vaporizer unit. The vaporizer unit has a wick member and heating member and is liquid-permeable such that liquid is conveyed from the tank through the vaporizer unit to the flow channel. The housing body has a cavity forming the tank and a wick member receiving chamber, and housing is divided by an intermediate wall and a flow channel section. An access opening from the receiving chamber to the flow channel is (Continued)

formed in the intermediate wall and covered by the heating member. Granular grains in the receiving chamber form the wick member and bear against the heating member. The grains form microchannels and are retained by a cover element. An access opening, covered with a liquid-permeable grid structure, establishes a liquid connection from the tank to receiving chamber in the intermediate wall.

9 Claims, 4 Drawing Sheets

(58) Field of Classification Search
CPC ........ A24F 40/46; A24F 40/50; A24F 40/485; A61M 11/041; A61M 11/042; A61M 15/06
See application file for complete search history.

(56) References Cited

U.S. PATENT DOCUMENTS

| | | |
|---|---|---|
| 2019/0246696 A1 | 8/2019 | Schmidt et al. |
| 2020/0093181 A1* | 3/2020 | Hubbard .............. A24B 15/403 |

* cited by examiner

VAPORIZER CARTRIDGE AND INHALER COMPRISING SUCH A VAPORIZER CARTRIDGE

CROSS-REFERENCE TO RELATED APPLICATIONS

This application is the U.S. National Stage of PCT/EP2020/066745 filed Jun. 17, 2020, which claims priority to German Patent Application No. 102019116726.4, filed Jun. 20, 2019, the content of both are incorporated herein by reference in their entirety.

FIELD OF THE INVENTION

The invention relates to a vaporizer cartridge as a component of an inhaler, comprising a housing body with a flow channel, a storage tank for storing liquid as well as a vaporizer unit comprising a wick member and a heating member, which vaporizer unit is formed to be liquid-permeable in such a manner that liquid can be conveyed at least initially in a capillary manner from the storage tank through the vaporizer unit in the direction of the flow channel.

The invention furthermore relates to an inhaler, configured and adapted for the inhalation of vapour enriched with active ingredients, comprising a cartridge carrier comprising at least one electronic control unit and an energy source as well as a vaporizer cartridge.

BACKGROUND OF THE INVENTION

Such vaporizer cartridges and inhalers are used in the luxury goods/stimulants industry, here in particular in the context of an electronic cigarette, what are known as an E-cigarette, and in the medical sector in order to be able to inhale liquid beverages and tobacco and/or liquid medical products in vapour form and/or as aerosols. During consumption, a person normally sucks on a mouthpiece of the inhaler, as a result of which a suction pressure arises in the flow channel, which suction pressure generates an air flow through the flow channel. The air flow can, however, also be generated by machine, for example, by a pump. In the flow channel, a liquid which is generated by the vaporizer unit and provided in a vaporised form is added to the air flow in order to administer an aerosol or an aerosol-vapour mixture to the consuming person. The liquid is stored at or in the vaporizer cartridge. Various mixtures with various components of the same or different vapour densities are used as the liquid. A typical mixture for use in an E-cigarette has, for example, components of glycerine and propylene glycol, where applicable, enriched with nicotine and/or almost any desired flavouring agents. The mixture can correspondingly have medical components and active ingredients for use in the medical or therapeutic sector, e.g. for the inhalation of asthma preparations.

The individual components of the vaporizer cartridge, namely the housing body having the flow channel, the storage tank and the vaporizer unit can be combined in a joint component, wherein this component is then a single-use article which is designed for a finite number of inhalations by a consuming person and together with a cartridge carrier as a reusable multi-use article which comprises at least one electronic control unit and an energy source forms an inhaler. The vaporizer cartridge can, however, also be formed by the joining together of several components, wherein individual components, e.g. the vaporizer unit or parts thereof, are arranged in the cartridge carrier as a multi-use article, and the storage tank as a separate component forms the single-use article. Finally, the inhaler can be used variably by replacing the single-use article which normally contains the liquid.

The single-use article and the multi-use article are correspondingly connected detachably to one another. The cartridge carrier as a multi-use article normally comprises at least one electronic control unit and an energy source. The energy source can be e.g. an electrochemical single-use battery or a rechargeable electrochemical battery, e.g. a Li-ion battery by means of which the heating member is supplied with energy via electrical contacts of the vaporizer unit. The electronic and/or electrical control unit serves to control the vaporizer unit within the vaporizer cartridge. The cartridge carrier can, however, also comprise components of the vaporizer cartridge. The single-use article can comprise the vaporizer cartridge or parts thereof and be formed so as to be capable of being plugged as a plug-on part onto the multi-use article or used as an insertion part into the multi-use article. Instead of a plug-type connection, screw connections, snap connections or other detachable quick connections can also be used. A mechanical and electrical coupling for the formation of a functionally ready inhaler is produced with the connection of single-use article and multi-use article.

The central component which ultimately determines the use (e.g. as an E-cigarette or as a medical inhaler) is the storage tank as a component of the vaporizer cartridge. This generally contains the liquid selected, desired and/or required by the person or a liquid mixture (also referred to generally below as fluid) as well as the housing body that forms or has the flow channel and the vaporizer unit. The fluid is stored in the storage tank of the vaporizer cartridge. The fluid is conveyed by means of the liquid-permeable vaporizer unit out of the storage tank as a result of at least initially capillary conveyance through the wick member and the heating member. The voltage generated by an energy source which is applied to the heating member leads to a flow of current in the heating member. As a result of the heating resistance, preferably the ohmic resistance of the heating member, the flow of current leads to a heating of the heating member and ultimately to a vaporization of the fluid located in the vaporizer unit. The gas or vapour generated in this manner escapes from the vaporizer unit in the direction of the flow channel and is recondensed to aerosol by mixing with the air flow. The fluid thus has a given path with a given direction of flow, namely as fluid through the wick member to the and through the heating member and as gas or vapour and/or aerosol out of the heating member into the flow channel. In the flow channel, the vaporized fluid is recondensed and carried along by the air flow if a pressure/vacuum acts on the flow channel, by virtue of the fact that e.g. a consuming person sucks on the flow channel or a pump conveys an air flow through the flow channel.

So that the fluid does not flow directly out of the storage tank into the flow channel, the vaporizer unit entirely covers the access from the storage tank to the flow channel. Entirely covers means in this context that the liquid is necessarily guided through the vaporizer unit so that the fluid cannot travel directly from the storage tank into the flow channel, but rather must take the "detour" via the wick member and the heating member. The wick member serves on the one hand the purpose of intermediate storage of fluid in order to still make available sufficient fluid for a few draws on the inhaler in particular in the case of an almost empty storage tank. The wick member serves on the other hand in particular the purpose of transporting the fluid from the storage tank in the direction of the flow channel as well as geometrically uniform supply of the heating member with liquid (synonym for fluid) and acts simultaneously as a type of non-return protection in order to prevent the return flow of fluid and/or vapour or gas in the direction of the storage tank.

Hitherto known vaporizer cartridges have a vaporizer unit with a wick member which is formed from several threads/fibres which are interwoven/twisted with one another composed e.g. of cotton wool or glass fibres. This fibre wick or fibre wicks connected in series have capillary properties which lead, upon initial contact with the fluid, to the fibre wick or fibre wicks dipping into the storage tank, and the fluid in the storage tank being absorbed and conveyed in the direction of the heating member. The heating member is normally formed in the form of a spiral-wound filament. This wound metal wire is composed, for example, of stainless steel, copper, copper compounds or nickel. This vaporizer unit can generally only be produced manually and has a limited storage capacity for intermediate storage of fluid. A further disadvantage lies in the low transport rate of fluid as a result of the limited number of microchannels and in the non-homogeneous temperature distribution which fundamentally arises over the longitudinal direction of the wick-spiral coil system with the risk of local overheating and the resultant generation of noxious substances. In other words, a uniform and continuous supply of the heating member with the fluid is only ensured to a limited extent.

SUMMARY OF THE INVENTION

The object on which the invention is thus based is to propose a compact vaporizer cartridge which ensures an improved liquid link between storage tank and heating member for constant and reproducible vaporizing conditions. The object furthermore lies in creating a corresponding inhaler.

This object is achieved by a vaporizer cartridge of the above-mentioned type in that the housing body is formed with a cavity, wherein the cavity of the housing body for the formation of the storage tank on the one hand and for the formation of a receiving chamber for the wick member on the other hand is divided by an intermediate wall having the flow channel at least in sections into two chambers, wherein at least one access opening from the receiving chamber for the wick member to the flow channel is formed in the intermediate wall, which access opening is entirely covered by the heating member, and a plurality of granular grains for the formation of the wick member bearing against the heating member are arranged in the receiving chamber, which plurality of granular grains preferably fill out the receiving chamber and as a result of their fill and/or formation form microchannels and are retained in the receiving chamber by a cover element, wherein at least one access opening for the establishment of a liquid connection from the storage tank to the receiving chamber is formed in the intermediate wall, which access opening is covered with a liquid-permeable grid structure.

The housing body is preferably formed with a continuous flow channel, which has at least one entry side $E_S$ and at least one exit side $A_S$, wherein the housing body is formed to be tubular with a cavity extending in a longitudinally axial manner and is divided by an intermediate wall having the continuous flow channel at least in sections into two chambers arranged consecutively in a longitudinally axial manner.

The term filling of the grains describes the grains lying next to one another both loosely and in a connected manner, wherein shaken and/or compressed arrangements of the grains are also covered by this term. The term formation of the grains describes, for example, that the grains themselves can have micro-cavities and/or microchannels. A plurality of random microchannels between the storage tank and the flow channel which ensure a constant and uniform vaporization on the exit side of the vaporizer unit are thus formed in the vaporizer unit between the individual grains lying next to one another and/or by individual grains. In other words, an optimum fluid coupling between the entry side into the vaporizer unit and the exit side out of the vaporizer unit is established by the granular wick member. A further significant advantage is seen in the fact that the granular material fills out the entire receiving chamber above the heating member, as a result of which an enlarged wick storage volume is provided in comparison with other wick solutions.

The mounting of a granular wick member is particularly advantageous since this can be adapted at the respective mounting location to any desired contour/geometry of the receiver of the wick member. As a result of the grain structure, the wick member is adapted, during mounting/filling of the granular material, flexibly to the respective contour/geometry and does not fill up cavities which form microchannels and avoids the formation of gaps to adjoining surfaces. As a result, a constant and reproducible liquid supply of the heating member and thus constant and reproducible vaporization conditions are ensured by the granular wick member. It does not play any role here whether the vaporizer unit—with the wick member and/or the heating member as a component of the vaporizer cartridge—is arranged on or in the cartridge carrier, i.e. on/in the multi-use article, or whether the vaporizer unit is arranged on/in the single-use article.

The vaporizer unit is advantageously a component of a multi-use article of the inhaler, while the storage tank is a component of a single-use article of the inhaler.

A preferred embodiment of the vaporizer cartridge is characterised in that the intermediate wall has, proceeding from a plate-like section which divides the cavity, with a section of the flow channel running preferably transverse to the longitudinal axis of the cavity, a channel-like section running through the storage tank with a section of the flow channel running preferably parallel to the longitudinal axis of the cavity for the formation of a vent, wherein the two sections of the flow channel are connected to one another and form a vapour chamber at their interface. In addition to a particularly compact design, this formation leads to improved vaporizing conditions as a result of the vapour chamber.

The channel-like section of the intermediate wall running preferably parallel to the longitudinal axis of the cavity advantageously runs centrally through the storage tank, wherein in each case an access opening for establishing a fluid connection from the storage tank to the receiving chamber is formed on both sides of the channel-like section of the intermediate wall in the plate-like section thereof, which access opening is covered with a liquid-permeable grid structure. The liquid connection between storage tank and heating member is thus optimised.

The heating member is preferably a MEMS component (Micro-Electro-Mechanical-System) which is composed substantially of silicon or has silicon or p- or n-doped silicon and, proceeding from an upper side facing the wick member down to a lower side facing the flow channel, has liquid- and vapour-permeable passages. A particularly effective formation of vapour can be achieved with this space-saving heating member.

A preferred further development of the vaporizer cartridge is characterised in that it is configured and adapted for mechanical and electrical connection to a cartridge carrier, for the formation of an inhaler, comprising at least one electronic control unit and an energy source, wherein the vaporizer unit comprises electrical contacts for electrical contact with the energy source. As a result of this, compact vaporizer cartridges/inhalers with constant and reproducible vaporizing conditions are created.

The object is also achieved by an inhaler of the above-mentioned type in that the vaporizer cartridge is configured and adapted described herein.

The advantages which arise from this were already described in conjunction with the vaporizer cartridge, hence reference is made to the above statements to avoid repetition.

DESCRIPTION OF THE DRAWINGS

Further expedient and/or advantageous features and further developments in relation to the vaporizer cartridge and the inhaler are apparent from the description. Particularly preferred embodiments of the vaporizer cartridge and the inhaler are explained in greater detail on the basis of the enclosed drawing. In the drawing.

DETAILED DESCRIPTION OF THE PREFERRED EMBODIMENTS

Figure 1:
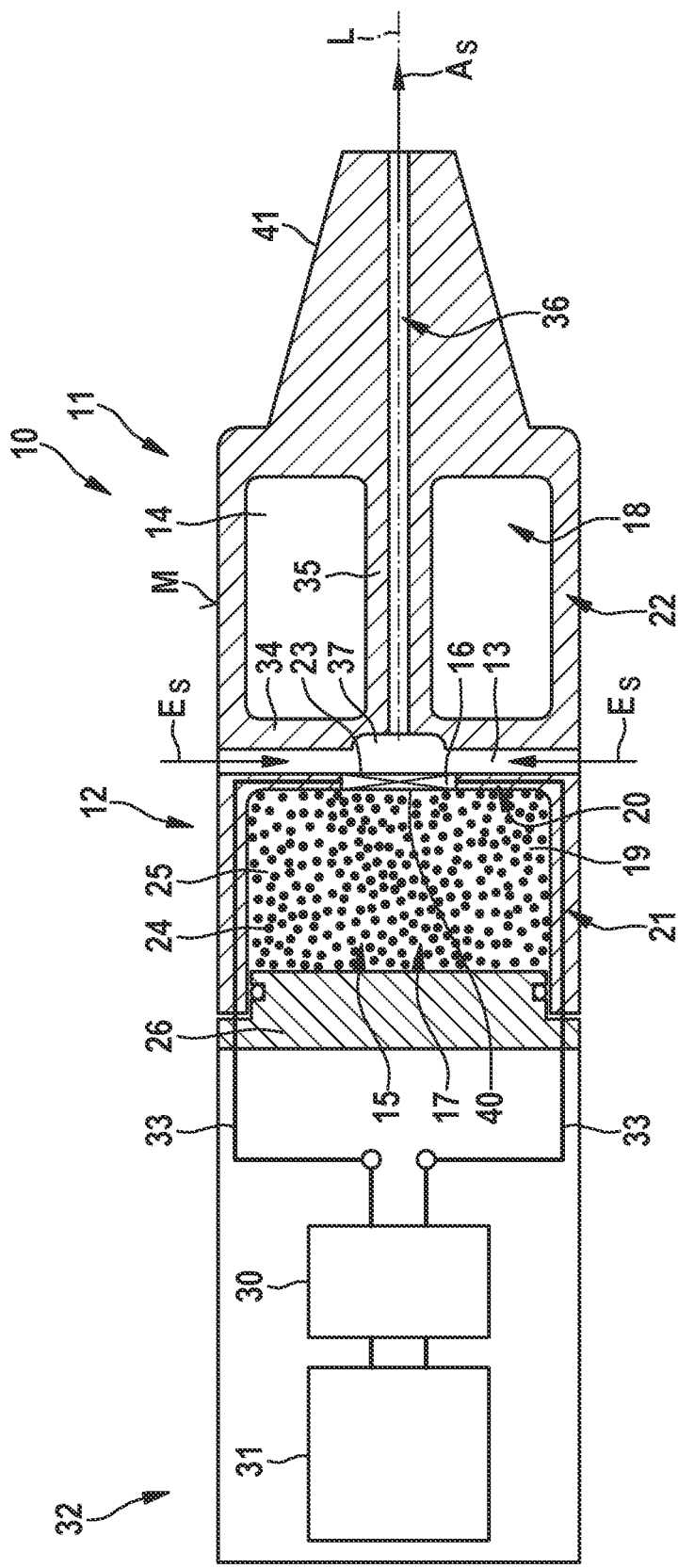
FIG. 1 shows a schematic representation of an inhaler with a vaporizer cartridge in section.
Figure 3:
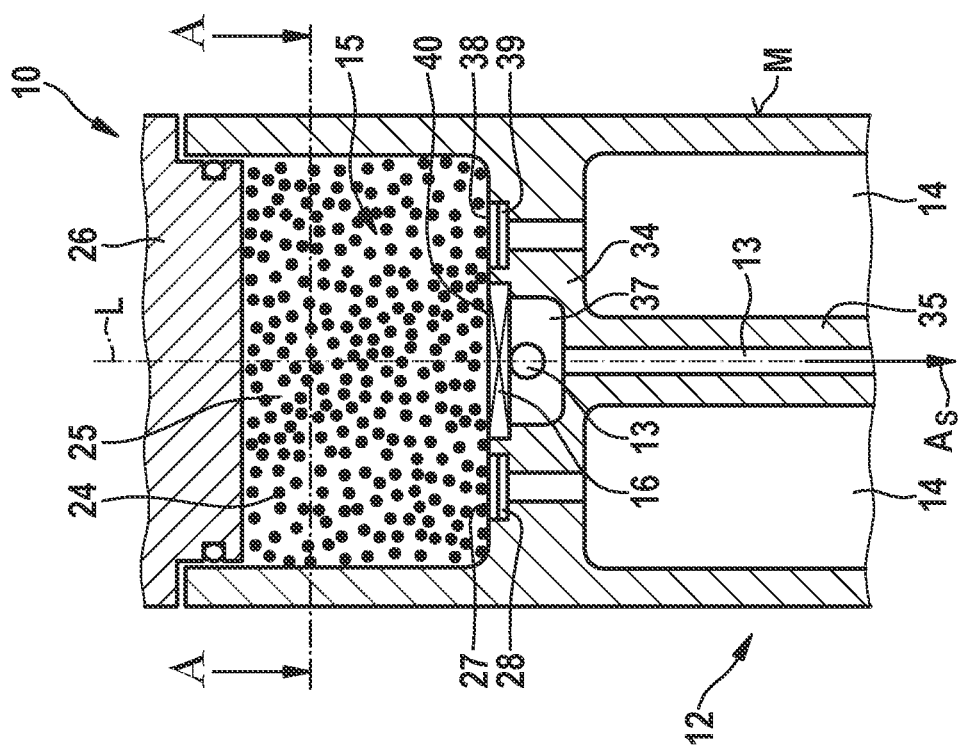
FIG. 3 shows the vaporizer cartridge according to FIG. 2 in a view rotated by 90° about the longitudinal axis.
Figure 2:
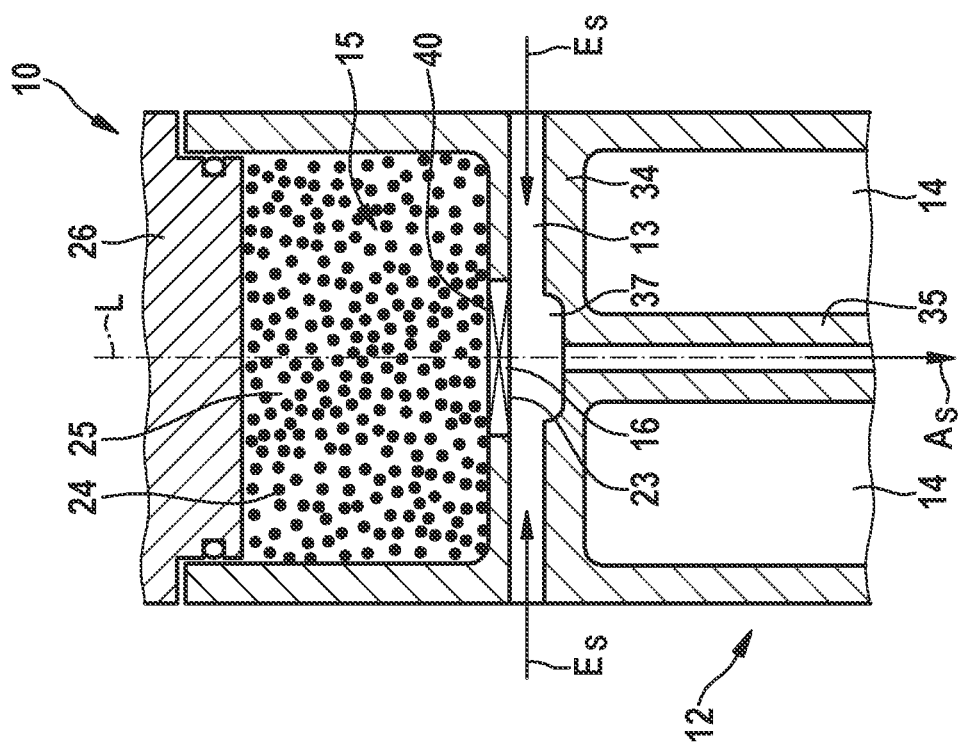
FIG. 2 shows key parts of the vaporizer cartridge according to FIG. 1.
Figure 4:
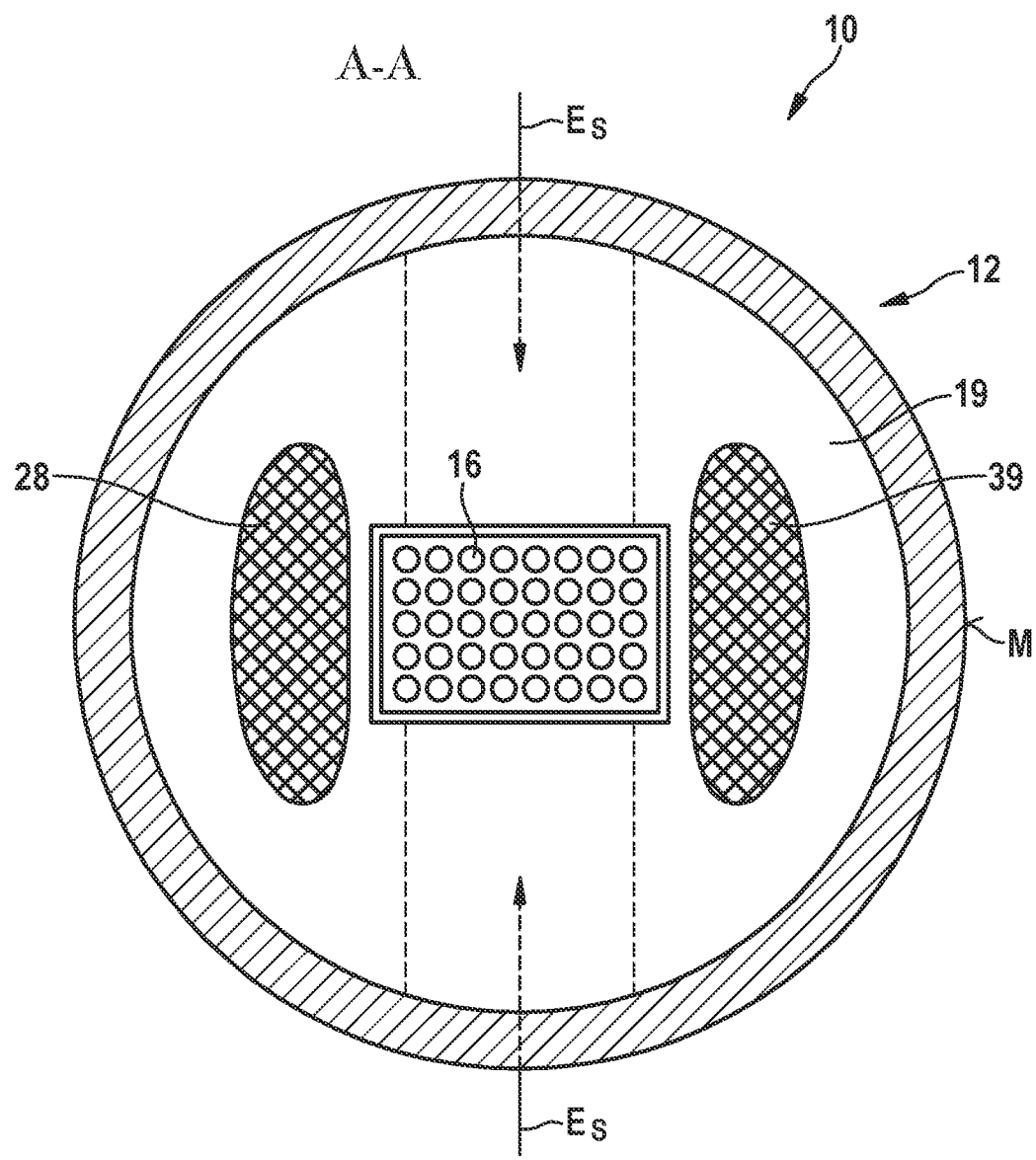
FIG. 4 shows the vaporizer cartridge according to FIG. 3 along section A-A.

The vaporizer cartridge represented in the drawing as well as the inhaler serve the purpose of inhalation of vapour enriched with active ingredients, e.g. nicotine, and/or aerosols from liquids and are correspondingly described in conjunction with an E-cigarette. The vaporizer cartridge and the inhaler can be used in the same manner to inhale vapour enriched with medical active ingredients from pharmaceutical products and/or food supplements.

The represented vaporizer cartridge 10 as a component of an inhaler 11 comprises a housing body 12 with a flow channel 13, a storage tank 14 for storing liquid as well as a vaporizer unit 17 comprising a wick member 15 and a heating member 16, which vaporizer unit 17 is formed to be liquid-permeable such that liquid can be conveyed at least initially in a capillary manner from the storage tank 14 through the vaporizer unit 17 in the direction of the flow channel 13.

This vaporizer cartridge 10 is characterised according to the invention in that the housing body 12 is formed with a cavity 18, wherein the cavity 18 of the housing body 12 for the formation of the storage tank 14 on the one hand and for the formation of a receiving chamber 19 for the the wick member 15 on the other hand is divided by an intermediate wall 20 having the flow channel 13 at least in sections into two chambers 21, 22, wherein at least one access opening 23 from the receiving chamber 19 for the wick member 15 to the flow channel 13 is formed in the intermediate wall 20, which access opening is entirely covered by the heating member 16, and a plurality of granular grains 24 for the formation of the wick member 15 bearing against the heating member 16 are arranged in the receiving chamber 19, which plurality of granular grains 24 preferably fill out the receiving chamber 19 and as a result of their fill and/or formation form microchannels 25 and are retained by a cover element 26 in the receiving chamber 19, wherein at least one access opening 27 for establishing a liquid connection from the storage tank 14 to the receiving chamber 19 is formed in the intermediate wall 20, which access opening 27 is covered with a liquid-permeable grid structure 28.

The housing body 12 is preferably formed with a continuous flow channel 13, which has at least one entry side $E_S$ and at least one exit side $A_S$, wherein the housing body 12 is formed to be tubular with a cavity 18 extending in a longitudinally axial manner and is divided by an intermediate wall 20 having the continuous flow channel 13 at least in sections into two chambers 21, 22 arranged consecutively in a longitudinally axial manner.

The cylindrical housing body 12 is formed to be closed towards one front side, namely to the front side onto which the cover element 26 is pushed, screwed or fastened in another manner. On the front side facing away from the cover element 26, the housing body 12 has at least one opening 29 which forms exit $A_S$ of the or each flow channel 13 which has at least one radially directed entry $E_S$ into the housing body 12 for the formation of the continuous flow channel 13.

The features and further developments described below represent, as seen on their own or in combination with one another, preferred embodiments. It is expressly pointed out that features which are summarised in the description and/or the drawing or are described in a joint embodiment can also functionally independently further develop vaporizer cartridge 10 described further above.

Figure 6:
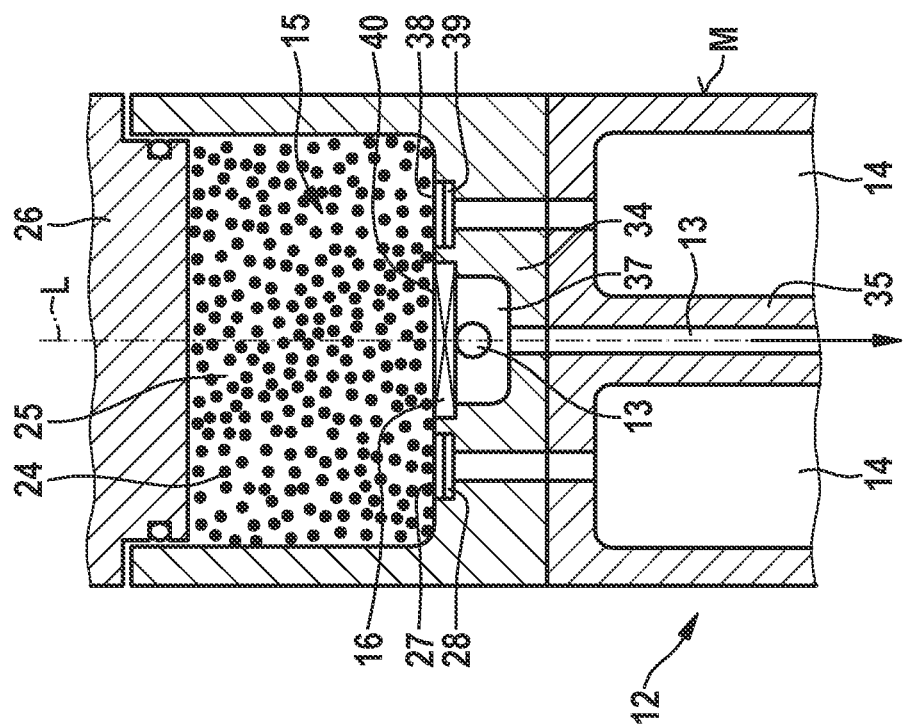
FIG. 6 shows the vaporizer cartridge according to FIG. 5 in a view rotated by 90° about the longitudinal axis.
Figure 5:
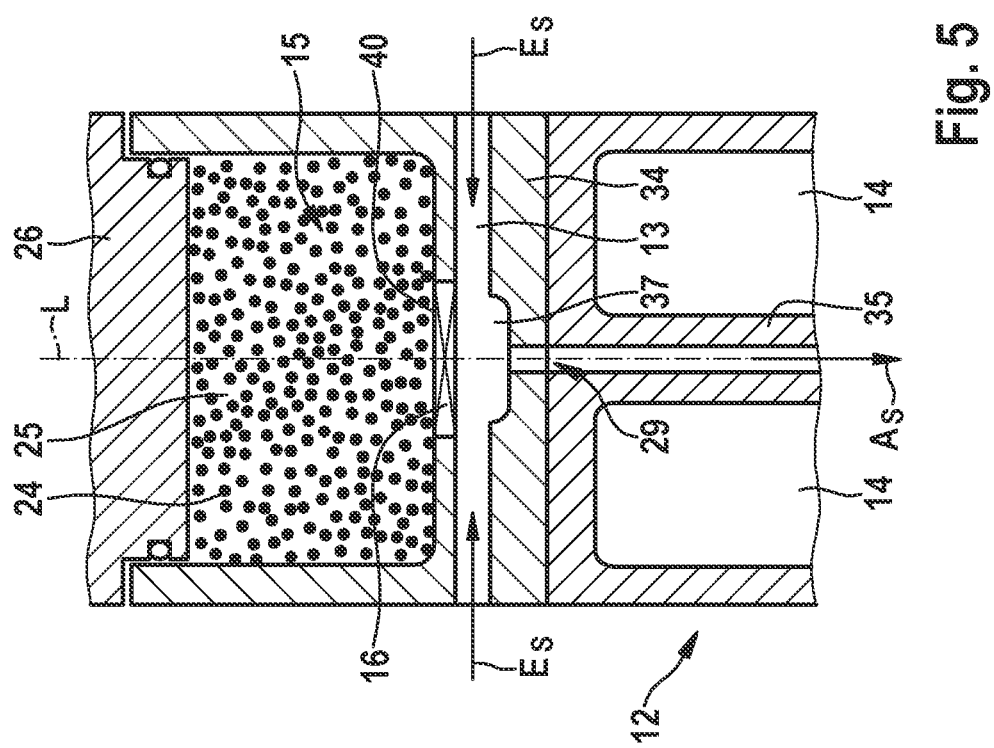
FIG. 5 shows a further embodiment of a vaporizer cartridge.

The vaporizer unit 17 is preferably a component of a multi-use article of the inhaler 11, while the storage tank 14 is a component of a single-use article of the inhaler 11. The vaporizer cartridge 10 is preferably formed as an independent module and single-use article. The vaporizer cartridge 10 can, however, also form a module entirely or partially together with other components. The vaporizer cartridge 10 is preferably configured and adapted for mechanical and electrical connection to a cartridge carrier 32 at least comprising an electronic control unit 30 and an energy source 31 for the formation of an inhaler 11, wherein the vaporizer unit 17 comprises electrical contacts 33 for electrical contact with the energy source 31. The inhaler 14 can be activated e.g. by an inhaling person, for example, as an E-cigarette, or be activated e.g. by a pump, e.g. as a medical instrument in the event that the person himself or herself can no longer suck or cannot suck to a sufficient degree. In the embodiment according to FIGS. 1 to 4, the cartridge carrier 32 has as a multi-use article only the control unit 30 and the energy source 31. The vaporizer unit 17 and the storage tank 14 are a component of the vaporizer cartridge 10 as a single-use or disposable article. In FIGS. 5 and 6, the single-use article is composed exclusively of the storage tank 14. By joining, plugging or the like of the storage tank 14 as a single-use article with or onto the vaporizer unit 17, which is a component of the cartridge carrier 32 as a multi-use article, the vaporizer unit 17 is formed.

As already mentioned, the vaporizer cartridge 10 comprises a continuous flow channel 13 with at least one entry side $E_S$ and at least one exit side $A_S$, wherein the term continuous describes that the flow channel 13 at the or each entry side $E_S$ and at the or each exit side $A_S$ is air-permeable. Two entry sides $E_S$ into the flow channel 13 are preferably formed in the figures. Optionally, however, only one entry side $E_S$ or more than two entry sides $E_S$ can also be provided and formed. The flow channel 13 or the flow channel section, which is formed in the intermediate wall 20 and is radially directed, i.e. runs transverse to the longitudinal axis L of the housing body 12, can continue e.g. in the lateral surface M of the housing body 12 parallel to the longitudinal axis L, preferably up to the exit side $A_S$ on the front side opposite the cover element 26. The intermediate wall 20 preferably has, proceeding from a plate-like section 34 which divides the cavity 18, with a section of the flow channel 13 running transverse to the longitudinal axis L of the cavity 18 or the housing body 12, a channel-like section 35 running through the storage tank 14 with a section of the flow channel 13 running preferably parallel to the longitudinal axis L of the cavity 18 or the housing body 12 for the formation of a vent 36, wherein the sections of the flow channel 13 are connected to one another and form a vapour chamber 37 at their interface.

The channel-like section 35 of the intermediate wall 20 running parallel to the longitudinal axis L of the cavity 18 or of the housing body 12 preferably runs centrally through the storage tank 14, wherein in each case an access opening 27, 38 for establishing a fluid connection from the storage tank 14 to the receiving chamber 19 is formed on both sides of the channel-like section 35 of the intermediate wall 20 in the plate-like section 34 thereof, which access opening 27, 38 is covered with a liquid-permeable grid structure 28, 39. The flow channel 13 can, however, also extend from the cover element 26 up to a mouthpiece 41.

The grains 24 can lie as a loose fill within the receiving chamber 19. In this case, even in the operating state of the vaporizer cartridge 10, the grains 24 can still move relative to one another and thus form variable microchannels 25. The grains 24 which lie next to one another and above one another are supported against one another. The grains 24 can strike against one another in a purely mechanical manner. The grains 24 can, however, also be toothed to one another mechanically between one another. The grains 24 of the wick member 15 can be formed to be identical and/or non-identical in terms of their material selection and/or their size. All grains 24 can have the same size, i.e. lie in a size range. The grains 24 can, however, have different sizes, i.e. lie in different size ranges. The grain size is preferably between 0.1 µm and 2 mm and particularly preferably between 3 µm and 300 µm. Purely by way of example, all grains 24 can lie in a size range between 50 µm and 100 µm (corresponds to a size range). The grains 24 of the wick member 15 can, however, also have locally different grain sizes. As a result of the selection of the grain sizes and the respective distribution e.g. in layers with grains 24 of different size ranges, among other things, the flow resistance of the wick member 15 can be set individually, ultimately even only during filling. The minimum grain diameter of the grains 24 in the fine-pore range should preferably be larger than the pores in the next roughest range in order to keep the pore gradient stable. As a result of the selection of the grain sizes used in a wick member 15, an individual pore gradient can be set for the wick member 15. The maximum grain size lies, depending on the flow properties of the liquid to be conveyed in each case, in each case outside a magnitude which rules out capillary conveyance. In other words, the grains 24 may only be of such a size that they still generate a capillary action as wick member 15. Equally, the grain diameter must not be smaller than the diameter of the capillaries or pores of the heating member 16 in order to avoid a blocking of the heating member 16 or an escape of grains 24 out of the heating structure.

All grains 24 can be composed of the same material. The grains 24 can, however, also be composed of at least two different materials. The grains 24 are preferably composed of sand (quartz) and/or graphite. Various other materials or mixtures of materials are, however, also possible as materials. Preferred materials for the grains 24 are e.g. PEEK granulate (polyetheretherketone granulate), PEK granulate (polyetherketone granulate), PA powder, VM17 granulate, glass, steatite, silicon dioxide, lignin, aerogel, viton, silicon, ash, charcoal, betonite, zeolite, diatomite, magnesium silicate, hard spar, diatomaceous earth, ground porphyr as well as mixtures thereof. The grains 24 of a wick member 15 are particularly preferably composed locally of different materials. For example, a layered structure of grains 24 composed in each case of the same material is understood as a local arrangement.

Various properties of the wick member 15 can be set by the selection of the materials of the grains 24 of a wick member 15. For example, grains 24 with different thermal conductivities can be used. The different material selection of the grains 24 also leads to it being possible to form the grains 24 to be e.g. compressible. Depending on the magnitude of the contact pressure with which the grains 24 are retained e.g. in the receiving chamber 19, the size of the pores of individual grains 24 or adjacent grains 24 can be actively influenced by elastic deformation. The vaporizer cartridge 10 can optionally be assigned a control member, by means of which, in the operating state of the vaporizer cartridge 10, the contact pressure on the wick member 15 can be set. The control member can be e.g. a lever element, a rotary element or any other pressing means.

Multi-layer wick members 15 can also be formed. In one embodiment, a first layer can be formed with grains 24 of a first type of grain. A second layer is formed with grains 24 of a second type of grain. A third layer is again formed with the first type of grain. The grains 24 of the second type of grain in the middle layer have a specific property which can be detected e.g. by means of a micro-controller of the control unit 30. During operation of the vaporizer cartridge 10, for example, a change in the wetting of the grains 24 in the second layer leads to a detectable change in the specific property of the second type of grain. This change is detected via the micro-controller which can be e.g. a sensor. It is then possible to make a regulatory intervention into the vaporization process by means of the control unit 30 in order to prevent e.g. what is known as a dry puff of the heating member 16.

The grains 24 of the wick member 15 can have the same or different geometrical shapes. The grains 24 can be, for example, needle-shaped, spherical, in the form of a grain of rice or also triangular. The grains 24 can have rounded edges or be formed with sharp edges. The term "grains" expressly does not refer to fibrous elements, i.e. does not refer to thin, fine, thread-shaped structures. For example, longitudinal and/or spherical pores can be formed depending on the respective shape of the grains 24 and their grain size. The pores can also be formed to be irregular. The grains 24 can also be at least partially magnetic. As a result of this, the grains 24 can be aligned e.g. during filling/pouring into the receiving chamber 19 by applying an external magnetic field in desired orientations. With the possibility of the alignment of the grains 24, for example, needle-shaped grains 24 can be oriented perpendicular to the flow channel 13, the properties of the wick member 15 can be determined individually in order to be able to use the wick member 15 e.g. as a non-return valve or as a control valve.

The wick member 15 which bears in an almost gap- and cavity-free manner against the heating member 16 has microchannels 23. The heating member 16 is formed to be liquid- and gas- or vapour-permeable. With its exit side, the wick member 15 bears against the entry side of the heating member 16 and forms a contact surface 40. The heating member 16 itself preferably has linear and/or non-linear passages which discharge into the flow channel 13. The heating member 16 can have a flat or curved formation or a formation shaped in a different manner. The heating member 16 is particularly preferably a MEMS component (Micro-Electro-Mechanical-System) which is composed substantially of silicon or has silicon or p- or n-doped silicon and, proceeding from an upper side facing the wick member 15 down to a lower side facing the channel 13, has liquid- and gas- or vapour-permeable passages. The minimum grain size of the grains 24 of the wick member 15 is, at least in the contact region 40 to the heating member 16, larger than the average diameter of the passages of the heating member 16.

The functional principle of the inhaler 11 according to the invention which comprises a vaporizer cartridge 10 according to the invention is described by way of example on the basis of an E-cigarette as an inhaler 11 in particular in relation to FIG. 1. A consuming person sucks e.g. on a mouthpiece 41 of the inhaler 11 which is formed from the cartridge carrier 32 and the vaporizer cartridge 10, wherein a liquid which contains, for example, glycerine, propylene glycol and possibly further active ingredients and/or flavourings is located in the storage tank 14 of the vaporizer cartridge 10. As a result of the sucking, a vacuum is generated in the flow channel 13, which vacuum itself activates the control unit 30 e.g. via a sensor, not represented. The control unit 30 controls the heating member 16 which is supplied with energy by the energy source 31. Liquid from the storage tank 14 is transported by means of the wick member 15 at least initially in a capillary manner through the microchannels 23 out of the storage tank 14 in the direction of the heating member 16. At or in the heated heating member 16, the liquid is converted into gas or vapour, wherein the heating member 16 transports the liquid or the vapour formed therefrom and/or aerosols as a result of the liquid- and gas- or vapour-permeable structure in the direction of the flow channel 13 and discharges it to said flow channel. The gas or the vapour and/or aerosols are formed during the mixing of the air flow in the flow channel 13 and are sucked in and inhaled by the consuming person.

The invention claimed is:

1. A vaporizer cartridge as a component of an inhaler, comprising:
    a housing body with a flow channel;
    a storage tank for storing liquid;
    a vaporizer unit comprising a wick member and a heating member, the vaporizer unit being formed to be liquid-permeable in such a manner that the liquid is conveyed at least initially in a capillary manner from the storage tank through the vaporizer unit in a direction of the flow channel;
    the housing body being formed with a cavity, the cavity of the housing body having a first chamber forming the storage tank and a second chamber forming a receiving chamber for the wick member, the cavity being divided by an intermediate wall;
    a section of the flow channel extending between the first and second chambers;
    a first access opening formed in the intermediate wall from the receiving chamber for the wick member, the first access opening being entirely covered by the heating member;
    a plurality of granular grains arranged in the receiving chamber form the wick member, the plurality of granular grains bearing against the heating member, the plurality of granular grains form microchannels as a result of their fill and/or formation; and
    a cover element retaining the plurality of granular grains in the receiving chamber;
    wherein a second access opening for establishment of a liquid connection from the storage tank to the receiving chamber is formed in the intermediate wall, the second access opening being covered with a liquid-permeable grid structure.

2. The vaporizer cartridge according to claim 1, wherein the plurality of granular grains fill out the receiving chamber.

3. The vaporizer cartridge according to claim 1, wherein:
    the flow channel is formed in the housing body as a continuous flow channel, the continuous flow channel having at least one entry side and at least one exit side;
    the housing body is formed to be tubular with the cavity extending in a longitudinally axial manner and divided by the intermediate wall and the section of the continuous flow channel, the first and second chambers being arranged consecutively in the longitudinally axial manner.

4. The vaporizer cartridge according to claim 1, wherein the vaporizer unit is a component of a multi-use article of the inhaler, while the storage tank is a component of a single-use article of the inhaler.

5. The vaporizer cartridge according to claim 1, wherein:
    the intermediate wall has a plate section which divides the cavity and a channel section running through the storage tank;
    the section of the flow channel runs transverse to a longitudinal axis of the cavity;
    a further section of the flow channel runs parallel to the longitudinal axis of the cavity for formation of a vent; and
    the section and the further section of the flow channel are connected to one another and form a vapour chamber at their interface.

6. The vaporizer cartridge according to claim 5, wherein:
    the channel section of the intermediate wall runs parallel to the longitudinal axis of the cavity and centrally through the storage tank; and
    further comprising a third access opening for establishing a fluid connection from the storage tank to the receiving chamber, the second access opening and the third access opening being formed on each side of the channel section of the intermediate wall in the plate section, the third access opening being covered with a liquid-permeable grid structure.

7. The vaporizer cartridge according to claim 1, wherein the heating member is a MEMS component (Micro-Electro-Mechanical-System) which is composed substantially of silicon or has silicon or p- or n-doped silicon and, proceeding from an upper side facing the wick member down to a lower side facing the flow channel, has liquid- and gas- or vapour-permeable passages.

8. The vaporizer cartridge according to claim 1, wherein the cartridge is configured and adapted for mechanical and electrical connection to a cartridge carrier, for the formation of an inhaler, the inhaler at least comprising an electronic control unit and an energy source, the vaporizer unit further comprising electrical contacts for electrical contact with the energy source.

9. An inhaler, configured and adapted for the inhalation of vapour enriched with active ingredients, comprising:
   a cartridge carrier at least comprising an electronic control unit and an energy source; and
   a vaporizer cartridge according to claim 1.

\* \* \* \* \*